United States Patent [19]

Müller et al.

[11] 4,409,400

[45] Oct. 11, 1983

[54] PROCESS FOR THE PREPARATION OF CYCLOHEXANE-1,3-DIONE FROM δ-KETOHEXANOIC ACID ESTER

[75] Inventors: Werner H. Müller, Eppstein; Karl E. Mack, Kelkheim; Hansjörg Hey, Hofheim am Taunus, all of Fed. Rep. of Germany

[73] Assignee: Hoechst Aktiengesellschaft, Frankfurt am Main, Fed. Rep. of Germany

[21] Appl. No.: 370,393

[22] Filed: Apr. 21, 1982

Related U.S. Application Data

[63] Continuation of Ser. No. 46,098, Jun. 6, 1979, abandoned.

[30] Foreign Application Priority Data

Jun. 8, 1978 [DE] Fed. Rep. of Germany ....... 2825170

[51] Int. Cl.$^3$ .............................................. C07C 45/54
[52] U.S. Cl. ..................................... 568/346; 502/38; 502/51
[58] Field of Search ......................................... 568/346

[56] References Cited

U.S. PATENT DOCUMENTS

| | | | |
|---|---|---|---|
| 3,932,511 | 1/1976 | Schaafsma et al. | 568/346 |
| 4,041,049 | 8/1977 | Muller et al. | 568/346 |
| 4,154,965 | 5/1979 | Meijer et al. | 568/772 |

*Primary Examiner*—J. E. Evans
*Attorney, Agent, or Firm*—Curtis, Morris & Safford

[57] ABSTRACT

Cyclohexane-1,3-diones are prepared by passing δ-ketocarboxylic acid esters in the gaseous phase over a temperature of from 250° C. to 500° C. at a catalyst. The catalyst contains at least one element of groups III B or IV B of the Periodic System in the form of a compound. Particularly preferred catalysts are thorium compounds on charcoal carriers.

6 Claims, No Drawings

PROCESS FOR THE PREPARATION OF CYCLOHEXANE-1,3-DIONE FROM δ-KETOHEXANOIC ACID ESTER

This is a continuation of application Ser. No. 46,098 filed June 6, 1979 and now abandoned.

The present invention relates to a process for the preparation of cyclohexane-1,3-diones by reacting δ-ketocarboxylic acid esters on catalysts.

Cyclohexane-1,3-diones are valuable starting materials of many syntheses. In particular, they may be converted by dehydrogenation into technically important resorcinols.

It has been known that cyclohexane-1,3-diones may be prepared by cyclization of δ-ketocarboxylic acid esters (German Offenlegungsschrift No. 2,245,270) or δ-enol lactones (German Offenlegungsschrift No. 2,261,751). The two processes are carried out in the liquid phase in the presence of strong bases and have the drawback that considerable amounts of useless inorganic salts are obtained and that large amounts of solvent are required.

Furthermore, it has been known that cyclohexane-1,3-diones may be obtained by a catalytic reaction of δ-ketocarboxylic acids (German Offenlegungsschrift No. 2,448,677) or of δ-ketocarboxylic acid esters (U.S. Pat. No. 3,932,511) in the gaseous phase. In the latter process the catalysts employed are materials which are thermally stable, have an inner surface of from 100 to 1500 m²/g and catalyze the cyclization reaction. Preference is given to charcoal, graphite and oxides of the alkaline earth metals, especially to charcoal.

However, the two last-mentioned processes have the drawback that the conversion rates of the starting compounds, especially of δ-ketohexanoic acid ester, are relatively low, so that the isolation of the cyclohexane-1,3-diones which are in most cases thermally unstable is only possible with a relatively high loss.

There has now been found a process for the preparation of cyclohexane-1,3-diones of the general formula

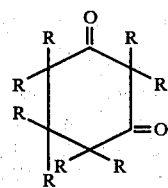

in which the individual radicals R may be identical or different and independently of one another may represent hydrogen, alkyl, cycloalkyl or aryl with the sum of all carbon atoms taken together being up to 12, by passing δ-ketocarboxylic acid esters of the general formula

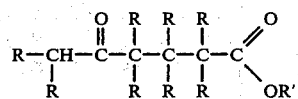

in which R is defined as above and R' is an alkyl, cycloalkyl or aryl radical of up to 9 carbon atoms, in the gaseous phase at a temperature of from 250° to 500° C. over a catalyst, wherein the catalyst comprises a carrier material onto which at least one element of groups III B or IV B of the Periodic System has been applied in the form of a compound. In this process the conversion rate of δ-ketocarboxylic acid esters—especially of δ-ketohexanoic acid ester—is considerably higher than in the above-mentioned process carrier out in the gaseous phase. The reaction pressure is not critical; the process is generally carried out at normal pressure, however, an excess pressure or low pressure may also be applied, a pressure range of from 0.1 to 10 bars being particularly suitable. The reaction temperature is preferably in the range of from 300° to 400° C.

Appropriate radicals R in the δ-ketocarboxylic acid ester are branched or linear alkyl radicals, for example methyl, ethyl, propyl, butyl, pentyl, hexyl, octyl, decyl and dodecyl. Suitable cycloalkyl groups are, for example, cyclopentyl, cyclohexyl, cyclodecyl or cyclododecyl. Preference is given to alkyl radicals or cycloalkyl radicals of up to 6 carbon atoms. As aryl radicals, there may be mentioned the phenyl and the naphthyl group. It is advantageous if in each case at least one of the radicals R bound to the same carbon atom represents hydrogen, preferably 6 of the 8 radicals being hydrogen; in the most preferred case, all 8 radicals R represent hydrogen.

The radical R' in the δ-ketocarboxylic acid ester is preferably a linear alkyl group or an aralkyl radical, such as benzyl, tolyl, phenylethyl, phenylpropyl. Particularly preferred groups are methyl, ethyl, n-propyl or n-butyl.

Of the elements of groups III B and IV B, i.e. scandium, yttrium, lanthanum and the lanthanides, titanium, zirconium, hafnium and the actinides, preference is given to lanthanum, the lanthanides, zirconium and thorium, the last-mentioned element being particularly preferred.

It is possible to apply several elements of the two above-cited groups of the Periodic System onto the carrier material, however, only one element is preferably employed. Besides the elements mentioned, also rubidium, strontium, aluminum, tin, lead, bismuth, molybdenum, manganese, rhenium, cobalt, copper, zinc and cadmium sometimes show a catalytic action.

The proportion of the elements of groups III B and IV B being applied onto the carrier material is generally in the range of from 0.05 to 10% by weight, preferably from 0.1 to 5% by weight, calculated on the catalyst.

The carrier material may be amorphous or crystalline and preferably shows an inner surface of from 50 to 1500 m²/g. There are suitable, for example, aluminum oxide, titanium dioxide, zirconium dioxide, alumosilicates, spinels, zeolites, aluminum oxide-chromium oxide or carbon. Preference is given to charcoal.

Thus, a particularly preferred catalyst is charcoal impregnated with a thorium compound.

By using the catalyst of the invention it is possible to obtain the cyclohexane-1,3-diones in a selectivity of more than 90%, with a conversion rate of from 45 to 50% of δ-ketocarboxylic acid ester, especially of δ-ketohexanoic acid ester. The reaction mixture obtained contains more than 35% by weight of cyclohexane-1,3-dione. Nearly 80% by weight of the cyclohexane-1,3-dione separates in a crystalline form and can be further purified.

The preparation of the catalyst is carried out by applying a compound of an element of groups III B or IV B (or several compounds of this kind) onto the carrier material according to one of the usual impregnation processes. Suitable metal compounds are for example those which are derived from acids containing oxygen, such as nitrates, sulfates, acetates, oxalates, furthermore halides, and compounds derived from C—H acid organic compounds (for example acetylacetone).

However, the anion is not critical.

For the impregnation process there may be used water or polar organic solvents, such as alcohols, ketones or nitriles; water being the preferred medium. Metal salts which are sparingly soluble in water may frequently be brought into an aqueous solution by complex-forming additives. Thus, for example, thorium oxalate in admixture with ammonium oxalate is readily water-soluble. In cases where additives of this kind are used, it is suitable to destroy the same by calcination following the drying of the catalysts. Depending on the type of carrier material and the additive used, temperatures in the range of from 400° to 700° C. in a nitrogen atmosphere are appropriate for the said purpose.

If necessary, the catalysts may be regenerated several times. This is effected by passing a gas mixture consisting of oxygen and another gas, for example nitrogen, carbon dioxide, steam or a noble gas, over the catalyst. Depending on the carrier material, the temperature is maintained at 150° to 600° C., preferably at 250° to 450° C. The oxygen content of the gas mixture is generally in the range of from 0.5 to 10% by volume, preferably from 1 to 5% by volume. A mixture of air and nitrogen is particularly suitable. After having been treated for several hours with the above-mentioned gas mixture, the catalyst has virtually regained its original activity.

The process of the invention is generally carried out by passing the gaseous δ-ketocarboxylic acid esters in a dilute state over the catalyst. The molar ratio of the diluent to the starting compound is from 1:1 to 50:1, preferably from 3:1 to 20:1.

Suitable diluents are in general gases, such as nitrogen, hydrogen, noble gas, carbon dioxide, water vapor and mixtures thereof in any proportions, evaporated organic solvents or mixtures thereof with nitrogen, hydrogen, noble gas, carbon dioxide or steam (proportion by volume of the organic solvent of 1 to 50%), and furthermore mixtures of nitrogen, noble gas, carbon dioxide or steam with air (proportion by volume of the air of 1 to 30%). Appropriate organic solvents are cyclic or acyclic ethers (such as tetrahydrofuran, 1,4-dioxan, diisopropyl ether), ethers of ethylene-glycols (for example dimethyl diethylene-glycol, diethyl diethylene-glycol, methylbutyl diethylene-glycol, ethylbutyl diethylene-glycol, dibutyl diethylene-glycol, methylethyl triethylene-glycol or dibutyl triethylene-glycol), esters of organic carboxylic acids (such as ethyl acetate, butane-1,4-diacetate and dimethyl succinate), as well as halogenated hydrocarbons (for example chloroform, carbon tetrachloride and 1,2-dichloroethane). A preferred diluent is a mixture of nitrogen and hydrogen (molar ratio of 1:1) or a mixture of nitrogen and an ether of the ethylene-glycols (molar ratio of 1:1).

For carrying out the process of the invention, the following mode of operation has proved to be particularly favorable: The reaction of the δ-ketocarboxylic acid ester is performed in a vertical reactor, the catalyst being present in its middle section. The starting compound is introduced into an evaporator—optionally being diluted with an organic solvent—then mixed with a mixture of hydrogen and nitrogen and passed over the catalyst. Since the pressure for the reaction is not critical, the process is carried out under normal pressure. At the reactor end, the reaction mixture is condensed in two stages, so that the main amount of the alcohol R'OH which is necessarily obtained is not condensed together with the cyclohexane-1,3-dione in the first stage, but only in the second stage. The cyclohexane-1,3-dione condensed in the first stage separates in a crystalline form upon further cooling.

COMPARATIVE EXAMPLE

A vertical reaction tube, whose middle section has been charged with 50 ml of carrier material, is heated to 350° C. A gas mixture of 10 standard liters of nitrogen, 10 standard liters of hydrogen and 1.5 standard liters of δ-ketohexanoic acid-methyl ester is introduced per hour from above into the reactor. As carrier materials, there are used successively granulated active charcoal, granulated aluminum oxide and extruded pieces of the oxides of aluminum, silicon, molybdenum, calcium, titanium, zirconium, lanthanum and thorium. The product discharged from the reactor is condensed and analysed by way of gas chromatography.

Table 1 indicates the conversion rates of δ-ketohexanoic acid-methyl ester and the selectivities of the formation of cyclohexane-1,3-dione (CD) during a test period of 40 hours.

TABLE 1

| Carrier material | Conversion rate in % | Selectivity in % |
|---|---|---|
| charcoal granulated | 12 | 82 |
| $Al_2O_3$ granulated | 10 | 73 |
| $Al_2O_3$ extruded pieces | 8 | 62 |
| $SiO_2$ extruded pieces | 7 | 58 |
| $MoO_3$ extruded pieces | 11 | 66 |
| CaO extruded pieces | 9 | 68 |
| $TiO_2$ extruded pieces | 10 | 74 |
| $ZrO_2$ extruded pieces | 8 | 73 |
| $La_2O_3$ extruded pieces | 9 | 65 |
| $ThO_2$ extruded pieces | 11 | 68 |

This Example shows that only a relatively small conversion rate of δ-ketohexanoic acid-methyl ester into cyclohexane-1,3-dione is obtained with unimpregnated carrier materials.

EXAMPLE 1

Granulated aluminum oxide (surface about 80 m$^2$/g) and granulated charcoal (surface about 1000 m$^2$/g), respectively, are impregnated with aqueous solutions of the nitrates of lanthanum, cerium, zirconium or a mixture of thorium oxalate/ammonium oxalate (weight ratio of 1:2), then dried for 6 hours at 120° C. and subsequently calcined for 6 hours in a nitrogen atmosphere at 420° C. The compounds mentioned are applied onto the carrier material in each case in an amount that the content of active elements (La, Ce, Zr, Th) in the catalyst is 1% by weight.

The results of the reaction of δ-ketohexanoic acid-methyl ester to give cyclohexane-1,3-dione (CD) under the same conditions as in the Comparative Example, however, during an operation period of 280 hours, have been summarized in Table 2.

TABLE 2

| | Carrier: $Al_2O_3$ | | Carrier: charcoal | |
|---|---|---|---|---|
| Element | Conversion rate in % | Selectiv. in % of CD | Conversion rate in % | Selectiv. in % of CD |
| La | 28 | 89 | 32 | 92 |
| Ce | 27 | 92 | 29 | 93 |
| Zr | 31 | 90 | 36 | 91 |

TABLE 2-continued

| Element | Carrier: Al₂O₃ | | Carrier: charcoal | |
|---|---|---|---|---|
| | Conversion rate in % | Selectiv. in % of CD | Conversion rate in % | Selectiv. in % of CD |
| Th | 37 | 94 | 48 | 95 |

This Example shows that the addition of the elements lanthanum, cerium, zirconium, but especially thorium, to the carrier materials Al₂O₃ and charcoal results in a considerable increase of the conversion rate and also in an improved selectivity, even over a prolonged period of time.

EXAMPLE 2

A catalyst is prepared by impregnating granulated charcoal with an aqueous solution of thorium nitrate and by drying and calcining it as has been described in Example 1. The finished catalyst contains 2% by weight of thorium and is employed for the reaction of δ-ketohexanoic acid-methyl ester to give cyclohexane-1,3-dione under the same conditions as in the Comparative Example.

After an operation period of 300, 600 and 900 hours the catalyst is regenerated by being treated in the reactor at a temperature of 380° C. during 5 hours with a gas mixture of nitrogen and air (1% by volume of oxygen). Subsequently the reaction is continued. The following conversion rates and selectivities for CD are obtained:

| | Operation period (hours) | | | | | | | | |
|---|---|---|---|---|---|---|---|---|---|
| | 10 | 300 | | 310 | 600 | | 610 | 900 | | 910 | 1200 |
| Conversion rate in % | 52 | 45 | Regeneration | 50 | 44 | Regeneration | 48 | 44 | Regeneration | 49 | 45 |
| Selectivity in % of CD | 88 | 92 | | 90 | 95 | | 90 | 93 | | 90 | 93 |

What is claimed is:

1. A process for the preparation of cyclohexane-1,3-dione consisting essentially of reacting, in the gaseous phase, a δ-ketohexanoic acid ester of the formula

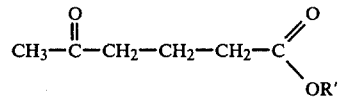

wherein R' is an alkyl having 1 to 4 carbon atoms at a temperature of from 250° C. to 500° C. in the presence of an impregnated catalyst consisting essentially of a catalytic carrier impregnated with a compound of an active component selected from the group consisting of lanthanum, zirconium, cerium and thorium.

2. The process of claim 1 wherein the δ-ketohexanoic acid ester is δ-ketohexanoic acid methyl ester.

3. The process of claim 1 wherein the active component of said impregnated catalyst is thorium.

4. The process of claim 1 wherein the catalytic carrier is carbon.

5. The process of claim 1 wherein the catalytic carrier is impregnated with 0.05% to 10%, relative to the catalyst weight, of said active component.

6. The process of claim 1 wherein the δ-ketohexanoic acid ester is diluted by adding 3 to 20 times the amount of an equimolar mixture of nitrogen and hydrogen or nitrogen and an ethylene-glycol ether.

* * * * *